United States Patent [19]

DeVor

[11] Plant 5,172

[45] Jan. 10, 1984

[54] ROSE PLANT NAMED DE VITE

[75] Inventor: Thelma G. DeVor, Pleasanton, Calif.

[73] Assignee: DeVor Nurseries, Inc., Pleasanton, Calif.

[21] Appl. No.: 425,047

[22] Filed: Sep. 27, 1982

[51] Int. Cl.[3] ..... A01H 5/00

[52] U.S. Cl. ..... Plt./23

[58] Field of Search ..... Plt./23

*Primary Examiner*—Robert E. Bagwill

*Attorney, Agent, or Firm*—Chas. W. Rummler

[57] ABSTRACT

A new white floribunda hybrid rose distinguished by its profuse production of medium sized blooms borne singly, and sometimes in clusters of 3 to 5 blooms resulting from side buds, the flowers being carried on a sturdy, upright peduncle about 4 to 6.6 cm. long and having long lasting quality both on the plant and as a cut flower. This plant flowers continuously, blooming freely in spring, summer and fall, and also in winter under glass; it has a vigorous and rapid free branching growth habit producing strong upright canes with abundant foliage and exhibiting clean white blooms throughout all seasons.

3 Drawing Figures

BACKGROUND OF THE INVENTION

This rose plant originated in 1974 as a seedling produced by me at Livermore, Calif. by crossing a stock variety, which resulted from a cross of Queen Elizabeth and an unnamed seedling, with Jack Frost (U.S. Plant Pat. No. 2,447) as the pollen parent with the object of obtaining a plant having the classical form, larger size and excellent stem of the seed parent and the excellent production of clean white color of Jack Frost so as to provide a good white rose for the greenhouse trade. Propagation of this new plant by budding through successive generations at Livermore, Calif. has shown that the aforesaid objectives have been accomplished and that the novel characteristics of the new plant hold true from generation to generation and appear to be firmly fixed.

DESCRIPTION OF THE DRAWING

My new rose plant is illustrated by the accompanying photographic drawings of which Sheet 1 shows in full color a face view of a newly opened flower and a plurality of buds in several stages of opening, and Sheet 2 shows upper and reverse sides of foliage, a bud about to open, and new and old wood, the color rendition of these drawings being as nearly true as it is reasonably possible to obtain by conventional photographic procedures.

DESCRIPTION OF THE NEW VARIETY

The following is a detailed description of my new rose plant based upon observation of plants grown at Pleasanton, Calif. in the spring and summer of 1982, the color designations being according the the R.H.S. Colour Chart published by The Royal Horticultural Society of London, England.

THE PLANT

Origin: Seedling.

Parentage:

*Seed parent.*—Seedling No. G64022/39.

*Pollen parent.*—Jack Frost (U.S. Plant Pat. No. 2,447).

Classification:

*Botanic.*—Hybrid Floribunda.

*Commercial.*—Greenhouse rose.

Form: Upright bush of compact shape.

Growth rate: Vigorously active.

Height: From ground level to flower about 155 cm. in about 4 months from planted bare root.

Growth habit: Free branching, vigorous and upright with strong canes.

Outside growth:

*From winter prune to mid-July.*—About 109 cm.

Cane length: Overall length of stem is in proportion to the size of the bloom.

*Color.*—Yellow green 146-B.

Foliage:

*Quantity.*—Abundant.

*Number of leaves.*—8 to 10 from hook on flower stem — spaced 3.5 to about 7.7 cm. apart.

*Form of leaf.*—Odd pinnate.

*Size of leaf.*—About 10 to 12.5 cm. long.

*Leaflets.*—3 to 7 in number. Size: Medium — varying from about 3.2 cm. wide and 4.4 cm. long to about 5.7 cm. wide by about 8.9 cm. long. Shape: Oval — with serrated margin. Texture: Leathery. Aspect: Smooth and slightly glossy. Color: Upper side — green 137-A. Under side — green 139-C. Ribs and veins: Prominent, slightly depressed on upper surface and slightly elevated on bottom side. Rachis: About 7.1 cm. for 7 leaflets and about 3.2 cm. for 3 leaflets, grooved on upper side and thorny on underside. Petioles: About 2 to 2.5 cm. including stipules. About 0.8 to 1 cm. wide and 1 cm. to about 1.3 cm. long.

Thorns: This plant has thorns which are dilated.

*Size.*—About 0.4 to 0.5 cm. at the base.

*Color.*—Yellow green 146-D.

THE BUD

Size: Medium.

*Form.*—Classical hybrid tea — urn-shaped and pointed.

*Diameter.*—About 1.5 cm. to 2.0 cm.

*Length.*—About 2.9 cm. to 3.4 cm.

Opening rate: Bud opens very slowly.

Color of petals:

*When sepals first divide.*—White 155-A.

*When petals begin to unfurl.*—White 155-A.

Sepals:

*Number.*—5.

*Shape.*—Mostly ovate and acuminate.

*Character.*—Sepals stand up when flower opens and then curl back, beginning to curl when bloom is half open.

*Color.*—Inside — Yellow green 145-B. Outside — Yellow green 144-B.

Calyx:

*Shape.*—Pear shaped.

*Size.*—Medium — about 0.9 to 1.1 cm. wide and about 1.1 to about 1.4 cm. long.

*Aspect.*—Smooth; calyx does not split.

Peduncle:

*Length.*—About 4 to 6.5 cm.

*Character.*—Erect, sturdy and upright with no tendency to nodding buds.

*Color.*—Green 143-B.

THE FLOWER

Blooming habit: Profuse and continuous — blooming freely in spring, summer and fall and also in winter under glass.

Size: Usually of medium size, but sometimes small.

*Diameter.*—When half to fully open, about 7.2 cm. to about 10.2 cm.

*Depth.*—About 2.7 cm. to about 3.8 cm.

Borne: Singly under glass, also sparingly in clusters of 3 to 5 blooms. When grown outside, flowers are borne singly and in clusters of 3 to 5 blooms.

Shape: When bloom first opens it is high centered and pointed; when bloom matures the petals reflex and quill.

Petalage:

*Number of petals.*—25 to 30.

*Arrangement.*—Imbricate and whorled.

*Form.*—Broadly round and acuminate with smooth margins and abrupt points at apex.

*Texture.*—Moderately leathery.

*Aspect.*—Satiny and velvety.

*Color.*—Outer petals: Body — White 155-A; Base — Yellow green 154-D and about 5 mm. wide at lowest part of base. Reverse side: Body — White 155-A; Base — Yellow green 154-D, colored area being about 3 mm. wide.

Petaloids:

*Number.*—3 to 8.

*Size.*—Small — about 0.4 cm. wide and 2.3 cm. long. Large — about 2.45 cm. wide and about 2.5 cm. long.

*Color.*—Body — Yellow 4-D; Base — Yellow 4-C.

Persistence: Flowers hang on and dry. Believe that flowers are moderately resistant to mildew, rust and black spot as observed in growing fields at Pleasanton and Glenn County, Calif.

Fragrance: Light.

Lasting quality: Long — both on plant and as cut flower.

REPRODUCTIVE ORGANS

Stamens:

*Number.*—About 110 to 130 in slightly introrse arrangement.

*Anthers.*—Size — about 1 mm. long. Color — Greyed orange 163-A.

*Filaments.*—Length — About 0.5 to 1.2 cm. Color — Yellow 2-C.

*Pollen.*—Color — Yellow 163-B.

Pistils:

*Number.*—About 90 to 110.

*Styles.*—Length: About 0.7 cm. to 1.4 cm. Color — Yellow green 154-C.

*Stigmas.*—Color — Grey yellow 162-D with a tint of red immediately below. Styles and stigmas extend or protrude about 0.3 cm. above the disc.

Ovaries: Covered with silvery white hair; styles unattached to each other throughout; and the calyx tube is ovid or egg shape.

FRUIT

Fertility: The fruit is fertile.

Shape: Globular but depressed at top.

Color at maturity: Yellow-orange 23-A.

I claim:

1. A new and distinct rose plant, substantially herein described, characterized by its profuse and continuous production of clean white flowers of generally medium size, with rapid growth rate and with vigorous, upright and free branching growth habit.

* * * * *

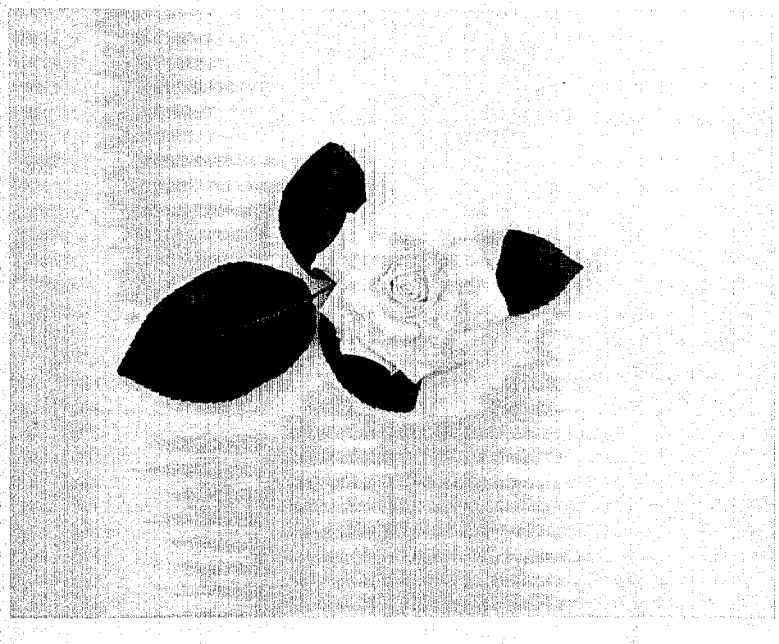
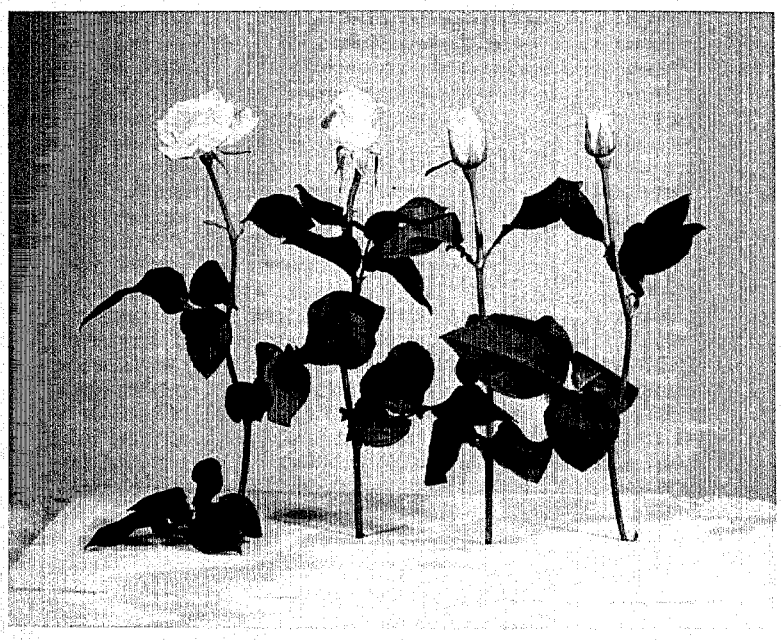

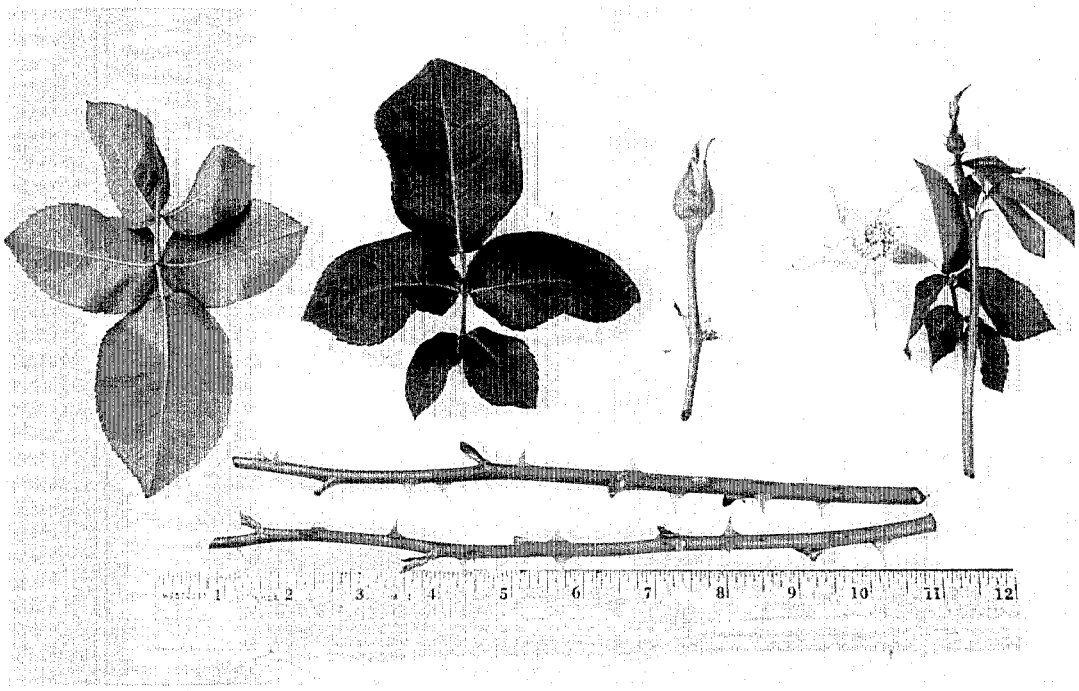
1
2
3
4
5
6
7
8
9
10
11
12